US008557050B1

(12) United States Patent
Gau et al.

(10) Patent No.: US 8,557,050 B1
(45) Date of Patent: Oct. 15, 2013

(54) SYSTEM FOR WASHING A SENSOR STRUCTURE

(75) Inventors: Jen-Jr Gau, Pasadena, CA (US); Chris Wiita, Pasadena, CA (US)

(73) Assignee: GeneFluidics, Inc., Irwindale, CA (US)

( * ) Notice: Subject to any disclaimer, the term of this patent is extended or adjusted under 35 U.S.C. 154(b) by 428 days.

(21) Appl. No.: 12/586,280

(22) Filed: Sep. 18, 2009

Related U.S. Application Data

(60) Provisional application No. 61/197,946, filed on Oct. 31, 2008.

(51) Int. Cl.
*B08B 3/02* (2006.01)
(52) U.S. Cl.
USPC .............................. 134/34; 134/172; 134/181
(58) Field of Classification Search
USPC .............. 134/34, 172, 180, 181, 186; 15/204, 15/302, 321
See application file for complete search history.

(56) References Cited

U.S. PATENT DOCUMENTS

| | | | | |
|---|---|---|---|---|
| 3,915,011 | A * | 10/1975 | Nelson | 73/864.35 |
| 4,675,053 | A * | 6/1987 | McCarty et al. | 134/21 |
| 4,896,047 | A * | 1/1990 | Weaver et al. | 250/573 |
| 5,028,865 | A * | 7/1991 | Meyrueix et al. | 324/96 |
| 5,271,164 | A * | 12/1993 | Yoshimura et al. | 34/105 |
| 5,460,041 | A * | 10/1995 | Andes et al. | 73/335.08 |
| 5,539,210 | A * | 7/1996 | Maarschalkerweerd | 250/372 |
| 6,123,820 | A * | 9/2000 | Bergkuist et al. | 204/411 |
| 6,145,521 | A * | 11/2000 | Wu | 134/104.4 |
| 6,843,110 | B2 * | 1/2005 | Deane et al. | 73/114.35 |
| 2002/0005440 | A1 * | 1/2002 | Holt et al. | 239/284.2 |

FOREIGN PATENT DOCUMENTS

| | | | |
|---|---|---|---|
| JP | 63-144211 | * | 6/1988 |
| JP | 07-325955 | * | 12/1995 |
| JP | 08-320291 | * | 12/1996 |
| JP | 09-198547 | * | 7/1997 |
| JP | 09-318420 | * | 12/1997 |
| JP | 2000-157942 | * | 6/2000 |
| JP | 2002-306006 | * | 10/2001 |
| KR | 2004013239 | * | 8/2002 |
| RU | 989422 | * | 1/1983 |

OTHER PUBLICATIONS

WIPO WO 94/00067 Jan. 1994.*

* cited by examiner

*Primary Examiner* — Michael Kornakov
*Assistant Examiner* — Benjamin L. Oserhout
(74) *Attorney, Agent, or Firm* — Gavrilovich, Dodd & Lindsey, LLP

(57) ABSTRACT

The system includes a wash source configured to concurrently generate a plurality of streams that are each incident on a sensor structure configured to detect a presence and/or amount of a compound on the sensor structure. The sensor structure has electrodes on a substrate. The wash source generates the streams such that each one of the streams is incident on a different one of the electrodes. Each of the streams is incident on one of the electrodes at an angle that is non-perpendicular to the sensor.

22 Claims, 19 Drawing Sheets

| WASH | TARGET (PG/ML) | SIGNAL (−nA) | STD DEV (−nA) | % ERROR |
|---|---|---|---|---|
| Manual Wash | 3000 | 70.18 | 23.13 | 32.96% |
| | 300 | 27.83 | 7.80 | 28.04% |
| | 30 | 25.20 | 10.10 | 40.08% |
| | NEG | 22.72 | 8.89 | 39.14% |
| Robotic Wash | 3000 | 68.39 | 6.84 | 10.00% |
| | 300 | 25.45 | 3.47 | 13.62% |
| | 30 | 19.95 | 2.50 | 12.54% |
| | NEG | 19.78 | 3.31 | 16.73% |

SYSTEM FOR WASHING A SENSOR STRUCTURE

RELATED APPLICATION

This application claims the benefit of U.S. Provisional Patent Application Ser. No. 61/197,946, filed on Oct. 31, 2008, entitled "System for Washing a Sensor Structure," and incorporated herein in its entirety.

BACKGROUND

1. Field of the Invention

The present invention relates to wash systems, and more particularly, to a system for washing a sensor structure.

2. Description of Related Art

A variety of chemical analyses such as biological assays are used to detect the presence and/or amount of one or more compounds in a sample. The analyses often make use of a sensor structure that includes one or more electrodes positioned on a substrate. During the analyses, one or more solutions are applied to the sensor such that one or more compounds within these solutions become bound to the sensor and/or to other compounds that are already bound to the sensor. Compounds that do not bind to the sensor or weakly bind to the sensor can reduce the reliability of these analyses. As a result, it is often desirable to use a wash to remove unbound or weakly bound compounds from the sensor.

In these wash steps, it is often difficult to achieve uniform washing of a single sensor and reproducible washing of different sensors. This lack of uniformity and reproducibility significantly reduces the quality of results that can be achieved with these analyses. Accordingly, there is a need for a wash that is suitable for use with chemical analysis.

SUMMARY

The wash system includes a wash source configured to concurrently generate a plurality of streams that are each concurrently incident on a sensor structure configured to detect a presence and/or amount of a compound on the sensor structure. The sensor structure has electrodes on a substrate. The wash source generates the streams such that each one of the streams is incident on a different one of the electrodes. Each of the streams is incident on one of the electrodes at an angle that is non-perpendicular to the sensor.

Another embodiment of the wash system includes a wash source configured to concurrently generate a plurality of streams that are each incident on a sensor structure configured to detect a presence and/or amount of a compound on the sensor structure. The sensor structure has electrodes on a substrate. The wash source generates the streams such that each one of the streams is incident on a different one of the electrodes. The wash source is configured to concurrently scan the streams across the surface of the electrode receiving the stream.

Another embodiment of the wash system includes a wash source configured to concurrently generate a plurality of streams that are each incident on a sensor structure configured to detect a presence and/or amount of a compound on the sensor structure. The sensor structure has electrodes on a substrate. The wash source generates the streams such that each one of the streams is incident on a different one of the electrodes. The wash source also includes one or more gas conduits that are each configured to apply a vacuum the sensor structure and/or blow a gas onto the sensor structure.

Another embodiment of the wash system includes a wash source configured to concurrently generate a plurality of streams that are each incident on a sensor structure configured to detect a presence and/or amount of a compound on the sensor structure. The sensor structure has electrodes on a substrate. The wash source generates the streams such that each one of the streams is incident on a different one of the electrodes. The wash source also includes one or more liquid absorbing media configured to be applied to the sensor structure so as to absorb a liquid from the sensor structure.

A method of operating a wash system includes concurrently spraying streams of a wash liquid onto a sensor structure having electrodes on a substrate. The streams are generated such that each one of the streams is incident on a different one of the electrodes.

BRIEF DESCRIPTION OF THE DRAWINGS

FIG. 1A is a topview of the sensor structure and FIG. 1B is a cross section of the sensor structure shown in FIG. 1A taken at the line labeled B.

DETAILED DESCRIPTION

A wash system is configured to apply a wash liquid to a sensor structure. The sensor structure has multiple electrodes on a substrate. The wash system is configured to concurrently generate multiple streams of a wash liquid. The wash system is also configured such that each of these streams can be concurrently received at a different one of the electrodes. As a result, each of the electrodes is concurrently washed with wash liquid. Additionally, the wash system can be configured such that each of the streams is incident on the electrode receiving that stream at about the same angle and pressure. As a result, each of the electrodes is washed under similar conditions which can enhance the reproducibility of the results.

In some instances, the wash system is configured such that each of the streams is incident on one of the electrodes at a non-perpendicular angle. The non-perpendicular angle can increase the shear force of the wash liquid across the electrode and can increase the efficiency at which compounds that are not bound to the electrodes or are weakly bound to the electrodes (non-specifically bound compounds) are removed from the electrodes.

Further, the wash system can be configured to concurrently scan the location where each stream is incident on an electrode across the surface of the electrode. Further, the scan can move toward an edge of the sensor structure in order to push the non-specifically bound compounds off of the sensor structure. The ability to scan the streams across the surface of the electrodes increases the uniformity with which each of the electrodes is washed.

The wash system can be employed with a variety of different sensing structures. For instance, a variety of sensing structures include electrodes on a substrate. The compounds bind to the electrodes and/or other compounds that are bound to the electrodes. The bound compounds can then be observed by detection of a fluorescent marker or other means. Other suitable sensors include assay chips. A preferred sensor structure includes multiple more electrochemical sensors arranged on a substrate. Electrochemical sensors can be used to detect the presence and/or amount of a target agent in a solution by generating electrical current from a chemical reaction in the solution and/or using electrical energy to cause a chemical reaction in the solution.

Figure 1A:
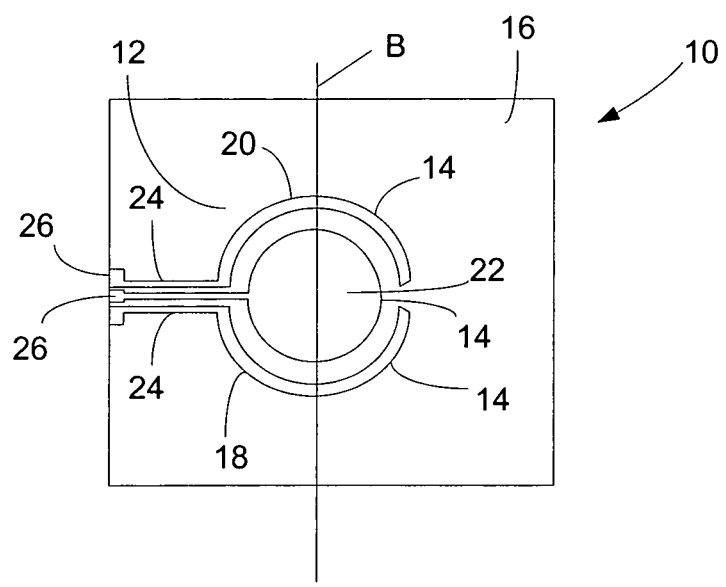
FIG. 1A through FIG. 1B illustrate an example of a portion of a sensor structure that includes an electrochemical sensor that is suitable for use with the wash system.
Figure 1B:
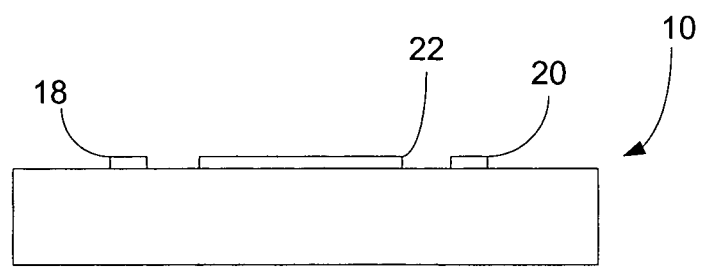

FIG. 1A through FIG. 1B illustrate an example of a portion of a sensor structure that includes an electrochemical sensor that is suitable for use with the wash system. FIG. 1A is a topview of the sensor structure 10 and FIG. 1B is a cross section of the sensor structure 10 shown in FIG. 1A taken at the line labeled B. The sensor structure 10 includes a plurality of electrodes 14 positioned on a substrate 16. A suitable substrate 16 includes, but is not limited to, a silicon substrate 16. Although the substrate 16 is shown as being constructed from a single material, the substrate 16 can have a composite construction.

The electrodes 14 include a reference electrode 18 and a counter electrode 20 positioned adjacent to a working electrode 22. In some instances, the counter electrode 20 and the reference electrode 18 are positioned on opposing sides of the working electrode 22. The counter electrode 20 and the reference electrodes 18 can have the same shape or can have different shapes. The counter electrode 20 and/or the reference electrode 18 can be positioned such that a portion of the working electrode 22 is positioned between different regions of the counter electrode 20 and/or between different regions of the reference electrode 18. Although the working electrode 22 is shown as having a round shape, the working electrode 22 can have a variety of other shapes including, but not limited to, rectangular shapes.

The reference electrode 18 can include a single layer of a conductive material such as a metal. For instance, the reference electrode can consist of a single layer of a metal such as gold, silver, copper, platinum, chromium, aluminum, titanium and nickel. The working electrode 22, the counter electrode 20, and the reference electrode 18 can be constructed of the same material or from different materials. Other suitable electrodes 14 include, but are not limited to, gold silver, copper, platinum, chromium, aluminum, titanium and nickel.

The working electrode 22 can be constructed such that the largest dimension of the working electrode 22 is less than 4 mm, 1 mm, 100 µm or 50 µm. Suitable widths for the counter electrode 20 and the reference electrode 18 include, but are not limited to, widths less than 20 µm, 100 µm, 0.5 mm or 3 mm. Suitable dimensions for the gap between the working electrode 22 and the reference electrode 18 and/or between the working electrode 22 and the counter electrode include, but are not limited to, gaps less than 1 µm, 100 µm, 0.5 mm or 2 mm. These dimensions can provide for a sensor 12 having a compact size that is suitable for use in on site assay equipment.

Figure 1C:
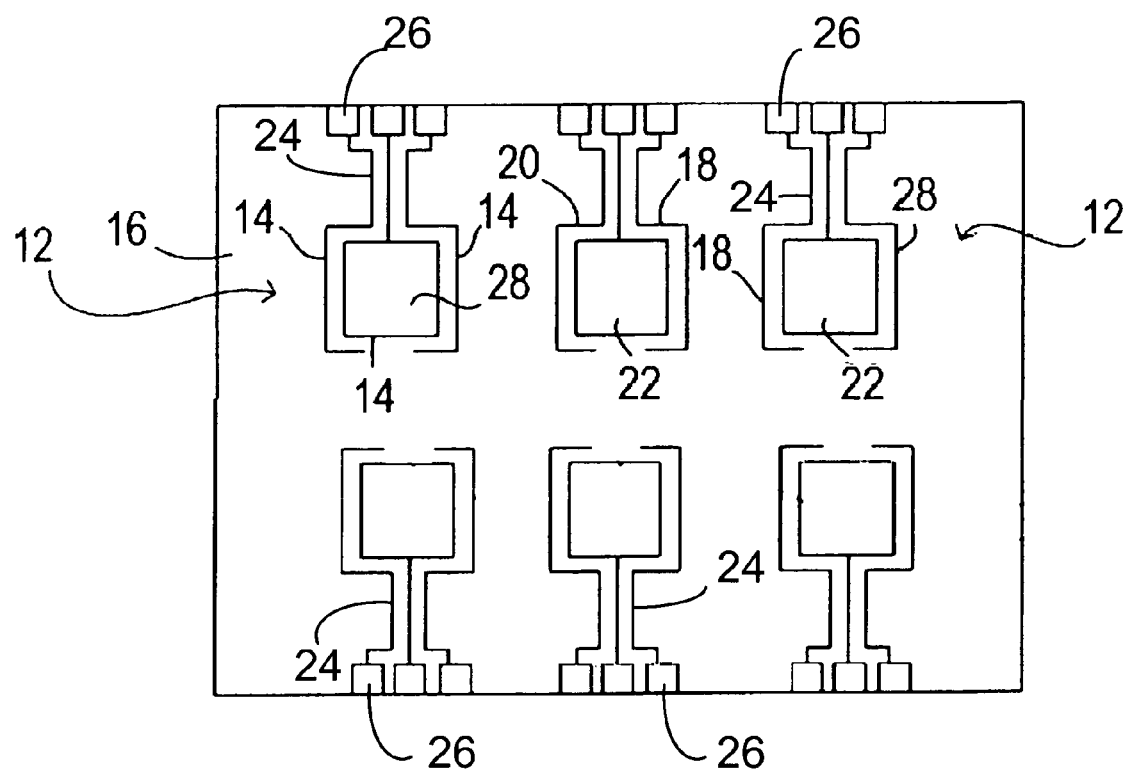
FIG. 1C illustrates a sensor structure having multiple electrochemical sensors where the sensors are constructed according to FIG. 1A and FIG. 1B.

Although FIG. 1A and FIG. 1B illustrate a portion of the sensor structure having a single sensor 12, a sensor structure 10 can include a plurality of sensors 12 as illustrated in FIG. 1C. The sensors 12 can be arranged in an array on the sensor structure 10. Each of the sensors 12 includes a working electrode 22, a reference electrode 18 and a counter electrode 20. Different sensors 12 on the sensor structure 10 can be employed concurrently or serially. Each sensor 12 can be employed to test for the presence and/or amount of a different target agent. As a result, the sensor structure 10 can provide highly efficient testing for a plurality of different target agents. Alternatively, multiple sensors 12 can be employed to test for the presence of the same target agent. The multiple tests can serve as a redundancy check or the tests performed on each sensor 12 can be for target agents from different sources.

Electrical conductors 24 on the substrate 16 can provide electrical communication between the electrodes 14 and contact pads 26. The contact pads 26 can be used to provide electrical communication between the electrodes 14 and external electronics. The electronics can then be employed to operate the sensors. For instance, the electronics can apply and/or receive electrical energy from the electrodes. In particular, the electronics can use the sensors to generate data for electrochemical experiments that identify the presence and/or amount of one or more target compounds on the sensor. A suitable method of operating the sensor of FIG. 1A through FIG. 1C as an electrochemical sensor is described in U.S. patent application Ser. No. 09/848,727, filed on May 3, 2001, entitled "Biological Identification System with Integrated Sensor Chip," granted U.S. Pat. No. 7,399,585, and in U.S. patent application Ser. No. 12/154,971, filed on May 28, 2008, and entitled "Chip Assay Having Improved Efficiency" each of which is incorporated herein in its entirety. Chemical analysis using biosensing assays requires a series of reagent introduction and washing such that free, uncomplexed soluble components are separated and removed from bound or complexed soluble components, prior to a next binding event or detection. The soluble components can be target molecules, reactants, non-reacting impurities or a signal reportor. Each reagent consists of components to be bound or to be reacted for each assay step with the carrying liquid or matrix. The removal of the free, uncomplexed, unbound components is done by applying, after the reagent is added, a wash liquid to the solid phase sensor array surface after the complexing reaction has occurred, to cause physical separation of the free labels from those that are bound. Such separation, in theory, leaves a volume on the solid phase sensor array surface in which the bound labels can be read free of the interference of the uncomplexed ones that are now washed away.

Figure 2:
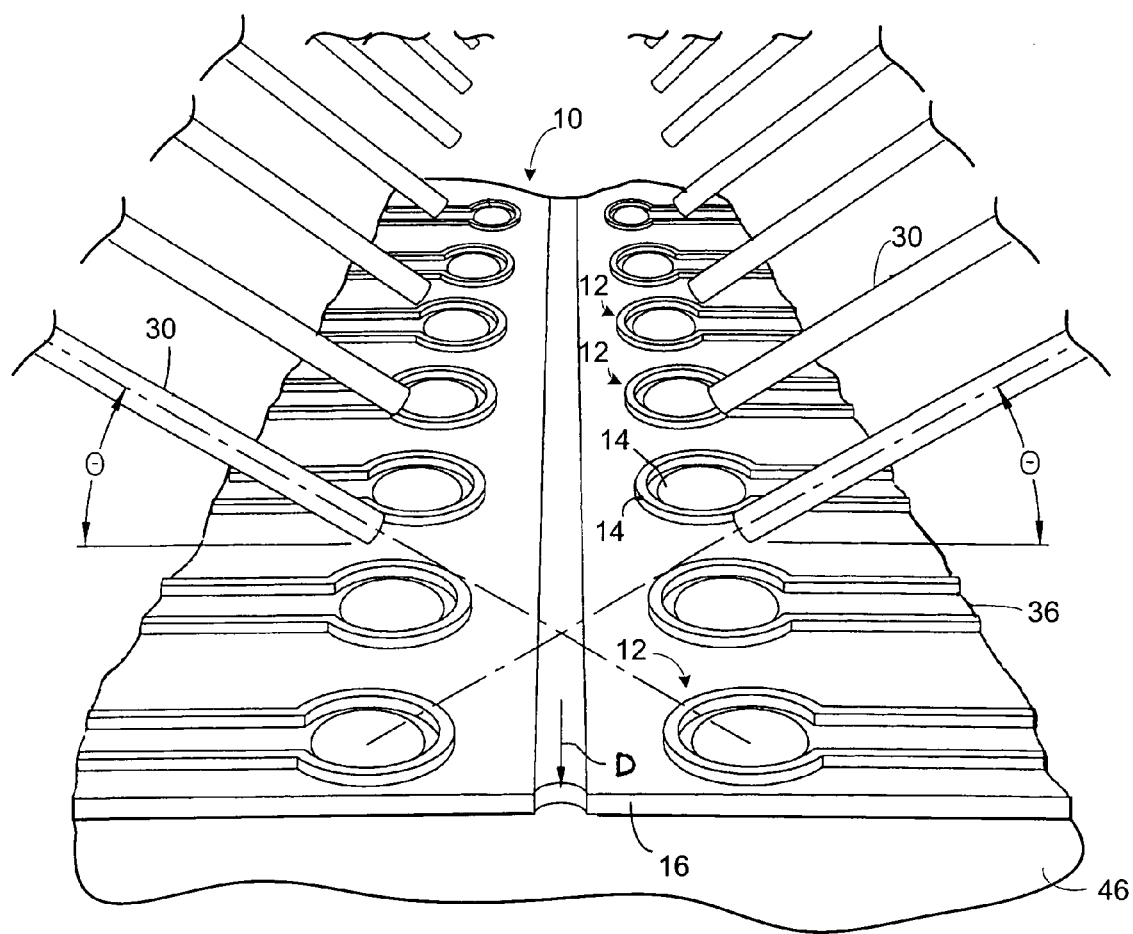
FIG. 2 is a perspective view of a wash system.
Figure 3:
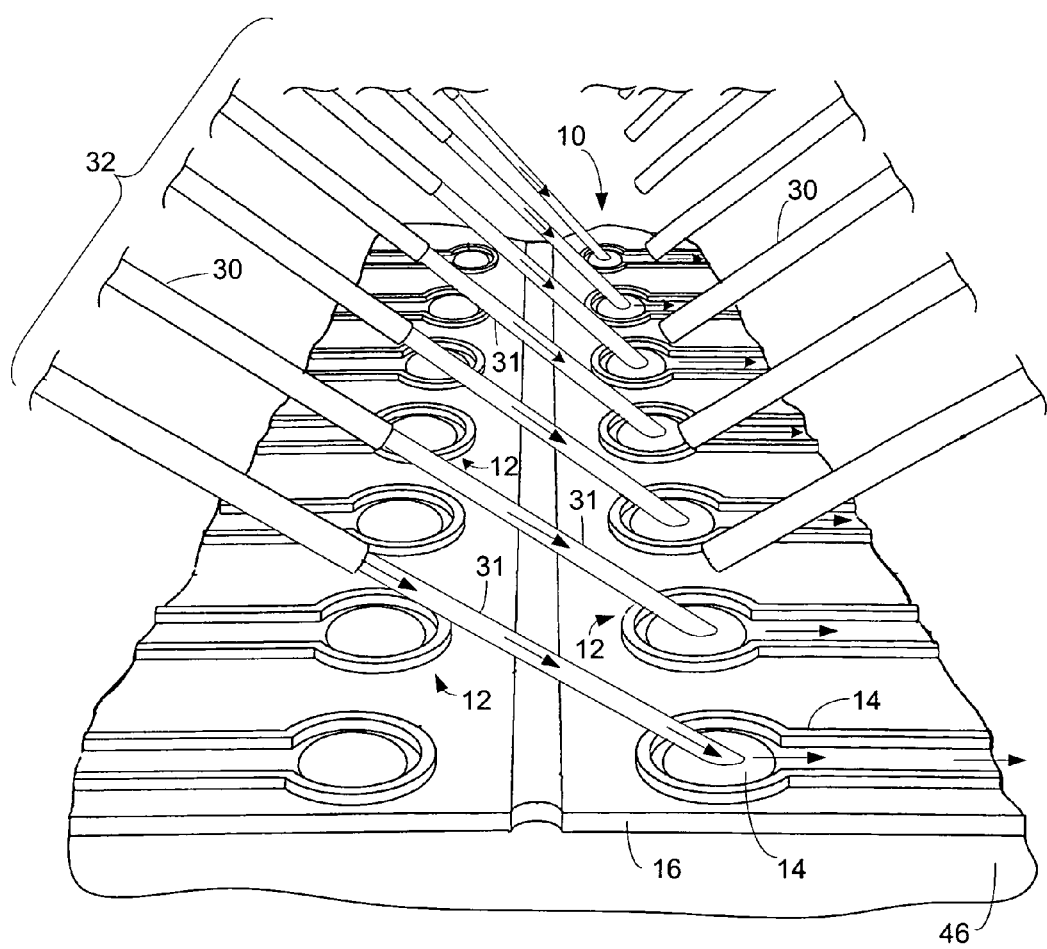
FIG. 3 is a perspective view of the wash system of FIG. 2 washing a sensor structure.
Figure 4:
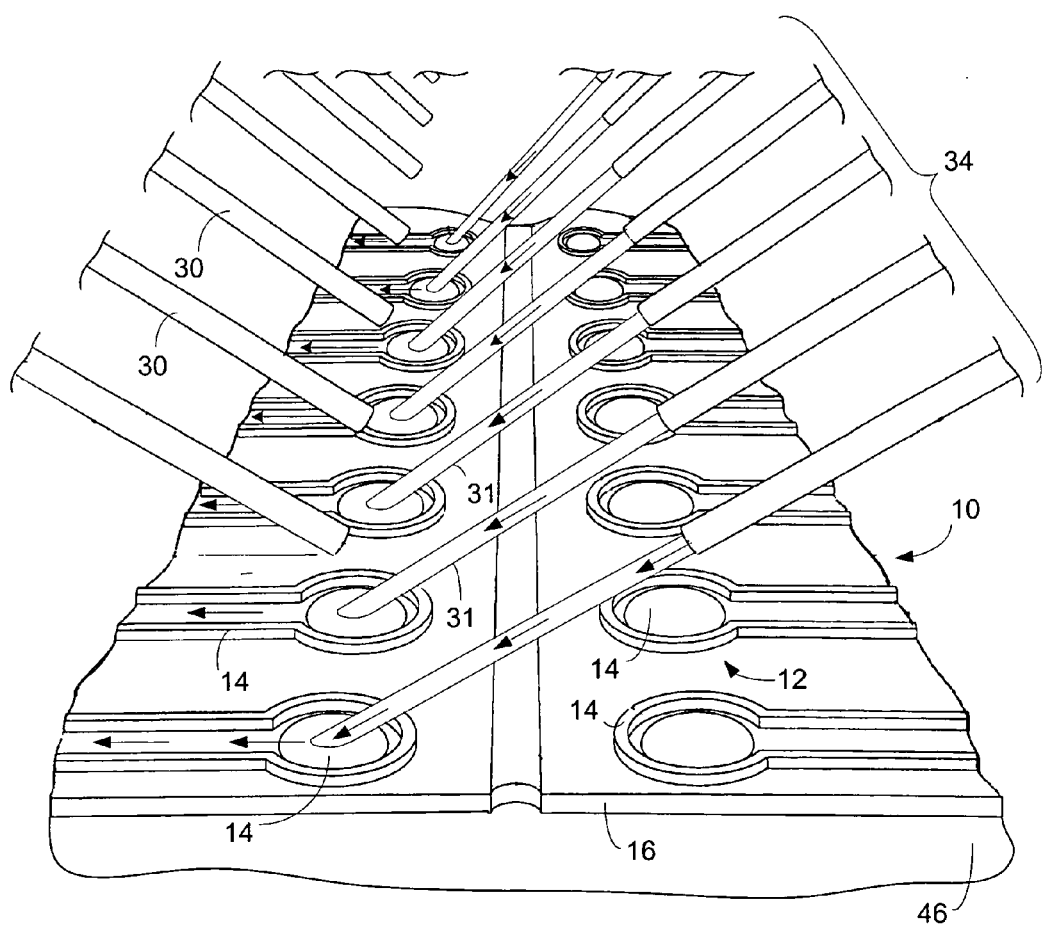
FIG. 4 is a perspective view of the wash system of FIG. 2 washing a sensor structure.

Wash systems are configured to wash non-specifically bound compounds off of the sensors. Examples of non-specifically bound compounds are compounds that are not bound to the sensors and/or compounds that are weakly bound to the sensor by bonds such as hydrogen bonds. The wash system can include a wash source configured to concurrently generate a plurality of streams 31 that are each incident on a sensor structure. For instance, FIG. 2 through FIG. 4 illustrate a wash system having a wash source that includes nozzles 30. Suitable nozzles 30 include a tube having a lumen extending through the tube. The wash source can be configured to generate streams 31 of a wash liquid by driving the wash liquids through the tubes.

The wash system of FIG. 2 through FIG. 4 includes a sensor structure having multiple electrodes positioned on a substrate. For instance, the wash system can include a sensor structure constructed according to FIG. 1A through FIG. 1C. The sensor structure can be placed on a holder 46 or platform that is configured to be moved relative to the nozzles 30 and/or the nozzles 30 can be moved relative to the holder 46 or platform. For instance, the sensor structure can be placed on a holder 46 or platform that is configured to move the sensor structure in the direction of the arrow labeled D in FIG. 2. The movement of the sensor structure and/or the nozzles 30 is such that the sensor structure can be positioned under the nozzles 30. The nozzles 30 are arranged such that the stream 31 from each nozzle 30 is incident on a different one of the electrodes. For instance, the nozzles 30 can be arranged such that each stream 31 is incident on an electrode included in a different one of the sensors. In particular, the nozzles 30 can be arranged such that each stream 31 is incident on a working electrode included in a different one of the sensors where each of the sensors is constructed according to FIG. 1A through FIG. 1C.

As is evident from FIG. 3 and FIG. 4, the wash system can optionally wash the sensor structure in at least two steps. In an early step, a first set of nozzles 32 of the wash system each concurrently generates a stream 31 of wash liquid that is incident on the sensor structure. After being incident on one of the electrodes, the wash liquid from each stream 31 flows off of the electrode that receives the stream 31 and then away from the electrode and away from the other electrodes. Since the wash liquid from each stream 31 flows away from the other electrodes, the wash liquid directed to each sensor does not come into contact with any other electrodes or sensors. In a latter step, a second set of nozzles 34 of the wash system of the wash system each concurrently generates a stream 31 of wash liquid that is incident on the sensor structure. After being incident on one of the electrodes, the wash liquid from each stream 31 flows over an edge of the sensor structure, carrying away non-specifically bound molecules. Since the wash liquid from each stream 31 flows over the edge of the sensor structure, the wash liquid directed to each sensor does not come into contact with any other sensor sensors.

In an alternative embodiment, the nozzles 30 can be arranged such that the streams 31 can be concurrently generated from the first set of nozzles 30 and the second set of nozzles 30 without the streams 31 contacting each other. In such embodiment, nozzles 30 and nozzles 30 can be offset, while maintaining spray angle θ, such that the concurrent streams 31 avoid contact and the wash liquid does not contacts a sensor other than the sensor that originally received the wash liquid.

In some instances, the wash source is configured such that the nozzles 30 can be moved vertically relative to the sensor structure and/or the sensor structure can be moved vertically relative to the wash source. As will be shown in more detail below, this vertical movement can be used to change the location where each stream 31 is incident on the sensor.

The nozzles 30 are positioned such that the streams 31 are incident on the sensors at non-perpendicular angles relative to the sensor. For instance, the nozzles 30 can be positioned such that the streams 31 are incident on the electrodes at non-perpendicular angles relative to the electrodes. In one example, the nozzles 30 are positioned such that they have an angle of incidence of the streams 31 on the sensor structure labeled θ. The angle of incidence (θ) may be greater than or equal to 5° and less than or equal to 80°, with one embodiment having a nozzle 30 angle position θ=40°.

Figure 5:
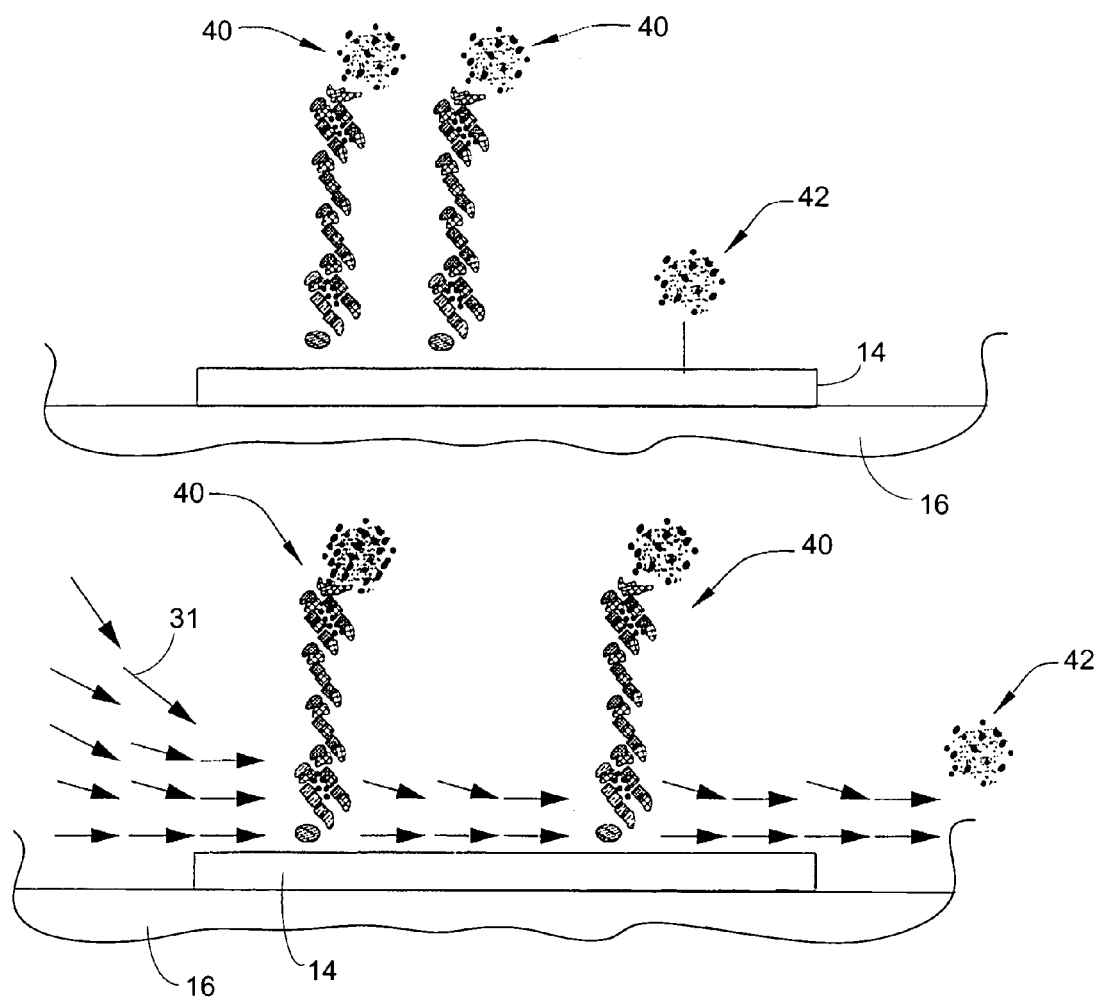
FIG. 5 illustrates the shear stress caused by the streams on compounds that specifically and non-specifically bound to a sensor structure.

FIG. 5 illustrates the shear stress caused by the streams 31 on non-specifically bound compounds 40 and specifically bound compounds 42. The non-perpendicular angle of the stream 31 relative to the sensors generates a shear stress on the sensors and particularly on the electrodes. The shear stress results in a shear flow force that is substantially horizontal relative to an upper surface of the sensor structure. Increasing the horizontal component of the force relative to the vertical component increases removal of the non-specifically bound compounds 40 and helps prevent collapsing or damaging the specifically bound compounds 42 that are typically bound through covalent bonds.

The wash source can also include gas conduits 44 in addition to the nozzles 30. The gas conduits 44 can be configured to blow a gas onto the sensor structure. The gas can be blown onto the sensor structure so as to blow excess wash liquid off of the electrodes, the sensors, and/or the sensor structure. Examples of suitable gasses for blowing onto the sensor structure include air. The gas conduits 44 can also be used to pull a vacuum. The vacuum can be applied to the sensors so as to vacuum excess wash liquid from the sensors.

Figure 6:
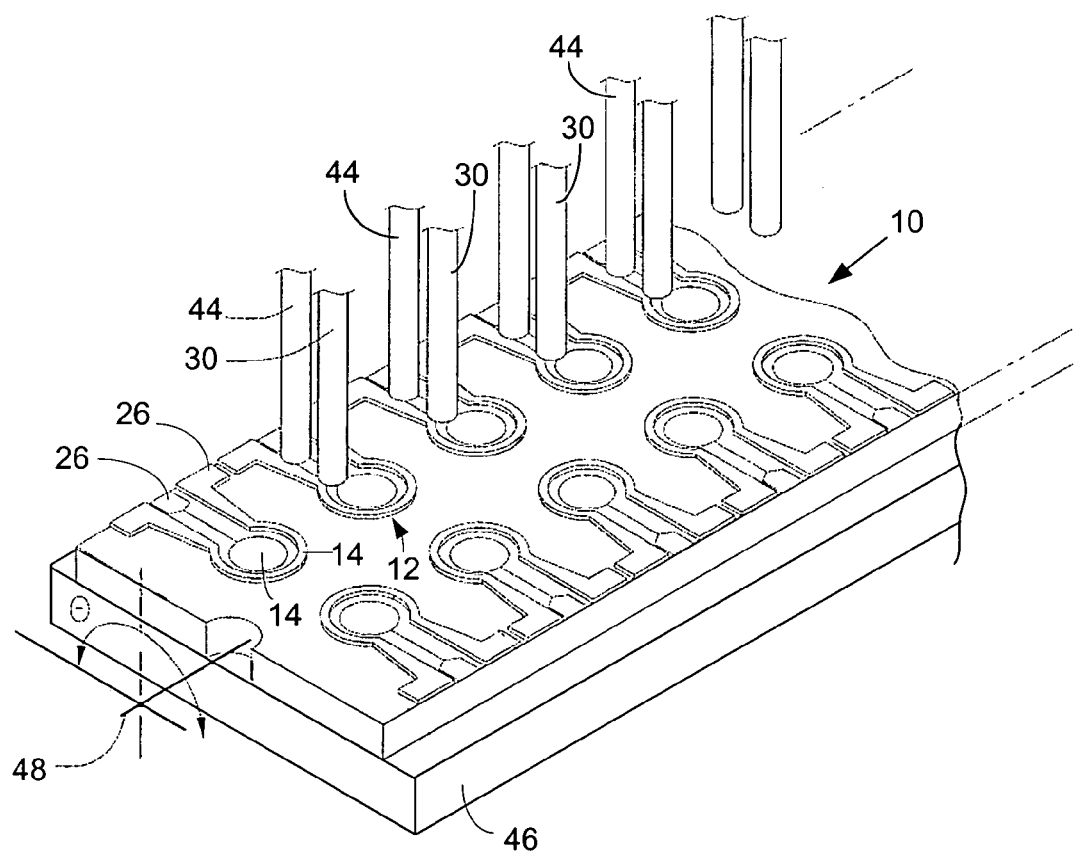
FIG. 6 is a perspective view of a wash system.

FIG. 6 is a perspective view of a wash system that includes both nozzles 30 and gas conduits 44. The gas conduits 44 are arranged such that different gas conduits 44 can be aligned with different electrodes on the sensor structure. For instance, the gas conduits 44 can each be aligned with an electrode included in a different sensor on the sensor structure.

The wash system can also include a platform or holder 46 configured to hold the sensor structure and rotate the sensor structure relative to the nozzles 30. The rotation can alter the angle of incidence (θ) of the streams 31 on the sensor structure. As a result, the angle of incidence (θ) can be changed to the desired angle. For instance, FIG. 6 illustrates the wash system including a platform configured to rotate the sensor structure about an axis 48. The angle of incidence (θ) of the streams 31 on the sensor structure is controlled by the rotation of the sensor structure about the axis 48. In an exemplary embodiment, the sensor structure is rotated about axis 48 such that the angle of incidence (θ) of the streams 31 on the sensor structure is greater than or equal to 5° and less than or equal to 80°, with one embodiment having a nozzle 30 angle position θ=40°.

The angle of incidence (θ) may be changed electronically or manually to optimize the washing process for particular arrangements of sensors on the sensor structure, wash liquids, and/or compounds. For instance, the platform in the wash system of FIG. 6 can be rotated electronically or manually. Alternately, the nozzles 30 can be adjusted to achieve a particular angle of incidence (θ). These nozzle 30 adjustments can be electronic and/or manual.

A method for operating a wash system can include: positioning the sensor structure under the nozzles 30; adjusting the wash system so as to achieve a particular angle of incidence (θ) such as an angle of incidence between θ=80° and θ=5°; spraying first streams 31 of wash liquid at the aligned electrodes; blowing gas at the aligned electrode and/or applying a vacuum to the aligned electrodes; adjusting the wash system so as to achieve a particular angle of incidence (θ) such as an angle of incidence between θ=80° and θ=5°; spraying second streams 31 of wash liquid at the aligned electrodes; and blowing gas at the aligned electrode and/or applying a vacuum to the aligned electrodes. The electrodes that receive the first streams 31 the first time can be the same or different from the electrodes that receive the second streams 31. Additionally or alternately, the, the second adjustment of the wash system so as to achieve a particular angle of incidence (θ). An example of this method applied to the operating the wash system of FIG. 6 includes the following steps: (1) positioning the sensor structure under the nozzles 30; (2) rotating the sensor structure clockwise between 10°) (θ=80° and 85°) (θ=5° from a horizontal position (θ=90°); (3) spraying a stream 31 of washing liquid at the aligned electrodes; (4) blowing air at the aligned electrodes; (5) rotating the sensor structure counterclockwise between 10°) (θ=80° and 85° (θ=5° from a horizontal position (θ=90°; (6) spraying a stream 31 of washing liquid at the aligned electrodes; and (7) blowing air at the aligned electrodes.

Figure 7:
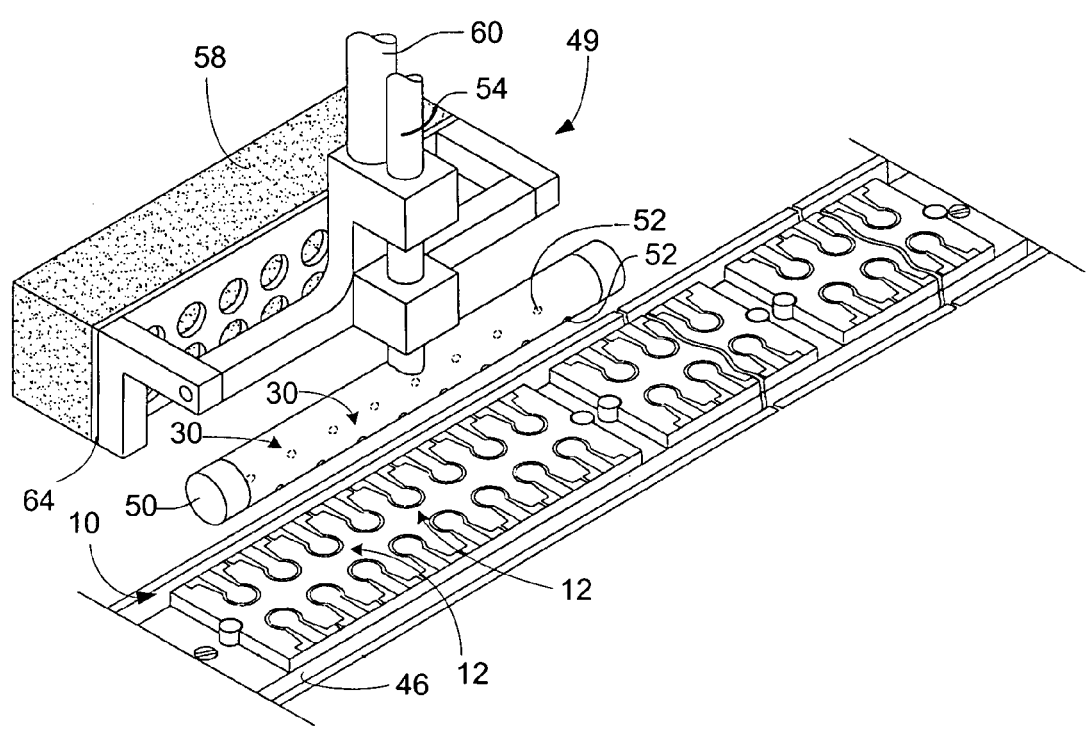
FIG. 7 is a perspective view of a wash system.
Figure 8:
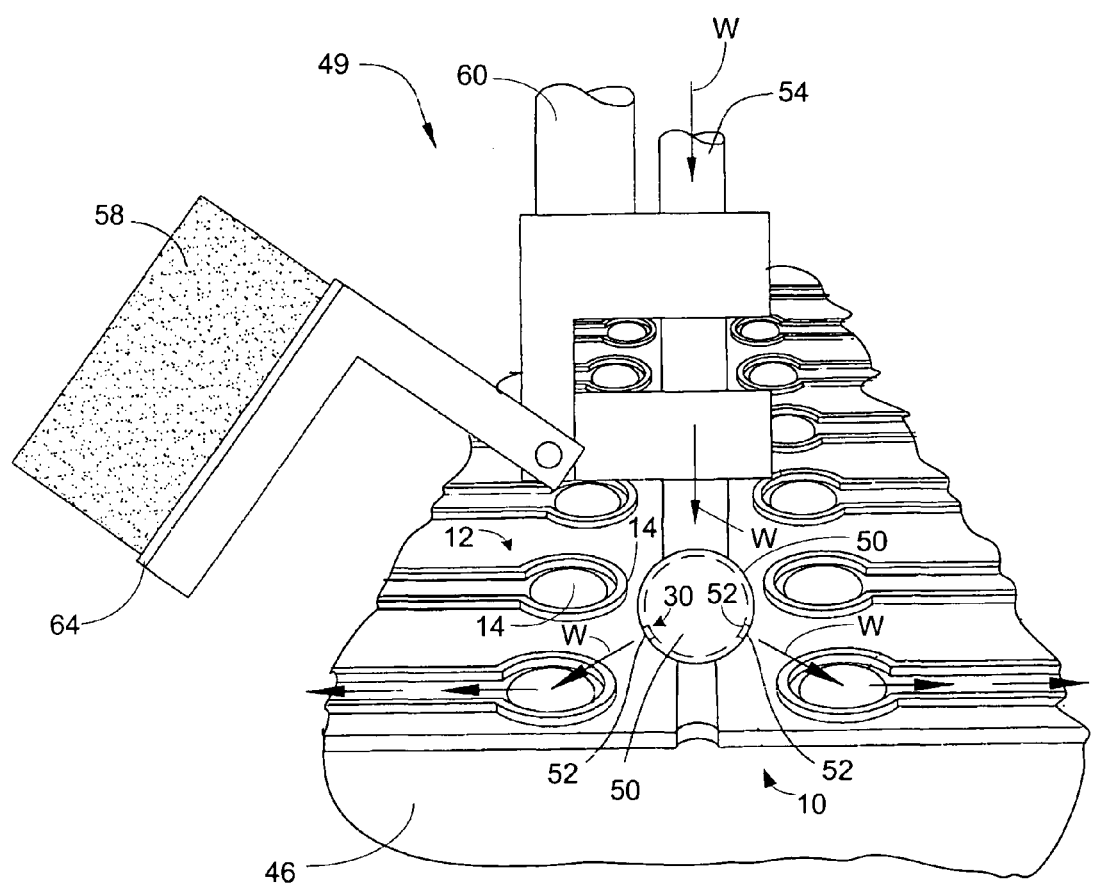
FIG. 8 is side perspective view showing the wash system of FIG. 7 washing a sensor structure.
Figure 9:
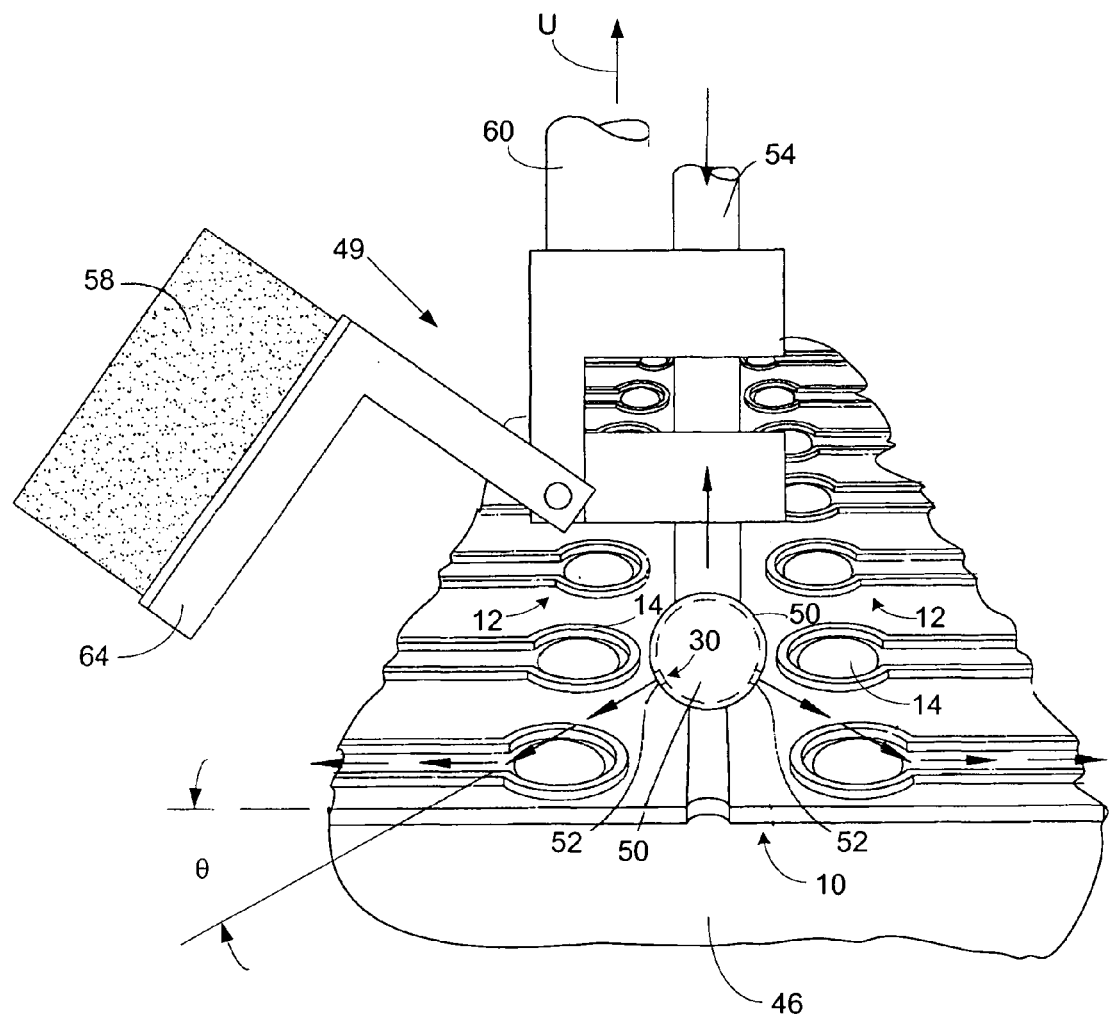
FIG. 9 is a side perspective view of the wash system of FIG. 7 washing a sensor structure.

Other structures can serve as nozzles 30. For instance, FIG. 7 is a perspective view of a wash system having a wash source 49 that includes a conduit 50 configured to receive a liquid in the interior of the conduit 50. Holes 52 extend through the sides of conduit 50. The conduit 50 can be in hydraulic communication with a secondary conduit 54 for delivering the wash liquid into the interior of the conduit 50. The wash liquid can be delivered into the interior of the conduit 50 at a pressure that causes the wash liquid to spray out of the holes 52 and form the streams 31. As a result, the holes 52 serve as the nozzles 30 from which the streams 31 are generated. The holes 52 can have similar or same geometries in order to provide each of the streams 31 with about the same pressure and accordingly apply each stream 31 to the electrode at about the same pressure.

The holes 52 are arranged such that different streams 31 are incident on different electrodes. For instance, the holes 52 can be arranged such that different streams 31 are each incident on an electrode included in different sensor. In some instances, the holes 52 are spaced apart from one another at a distance equal to the distance between the electrodes on the sensor structure that are each to receive one of the streams 31.

In addition to the gas conduits 44 or as an alternative to the gas conduits 44, the wash system can include a water absorbing medium that the wash system can apply to the sensor structure so as to remove liquid from the sensor structure. Examples of suitable water absorbing media include, but are not limited to, porous media such as sponges. For instance, the wash system of FIG. 7 includes a wash source 49 that includes a sponge 56 that serves as a water absorbing medium. The conduit 50 and the sponge 56 are each connected to an arm 60 that can move vertically.

FIG. 8 through FIG. 11 illustrate operation of the wash system of FIG. 7. The wash system includes a holder 46 or platform on which one or more sensor structures are placed. The wash system can operate the holder 46 or platform so as to align the sensor structure with the wash source 49 as is evident in FIG. 8. The arm 60 can be moved downward in order move the wash source 49 downward and align the holes 52 with the electrodes or sensors on the sensor structure. Wash liquid is delivered into the interior of the conduit 50 such that the streams 31 are generated as illustrated by the arrows labeled W. In one example, the holes 52 are aligned with the sensor structure such that each stream 31 of wash liquid initially strikes a center of a different electrode on the sensor structure. In another exemplary embodiment, the holes 52 are aligned with the sensors or electrodes such that each stream 31 of wash liquid initially strikes a center of a different electrode on the sensor structure. In the latter embodiment, a smaller vertical force (perpendicular to the surface of the sensor structure) can initially be applied to the sensors or electrodes than in the previous embodiment.

The arm 60 can be moved vertically through the use of electronic control. As a result, the height of the nozzles 30 can be electronically controlled. Changing the vertical position of the nozzles 30 permits the location where each stream 31 strikes the sensor structure to be controlled and, in some instances, altered during generation of the streams 31. For instance, as illustrated by the arrow labeled U in FIG. 9, the arm 60 of the wash system can be raised while still maintaining a stream 31 of wash liquid. As the arm 60 is raised, the stream 31 of wash liquid strikes progressively closer to an edge of the sensor structure and effectively drives non-specifically bound compounds off of the electrodes and/or off of the sensors.

The holes 52 are positioned such that they are angled φ° from a horizontal position. The hole 52 angle position φ may be greater than or equal to 5° and less than or equal to 80°. In an exemplary embodiment, the hole 52 angle position φ may be changed manually to optimize the washing process for particular arrangements of sensors, reagents, and/or soluble components.

Figure 10:
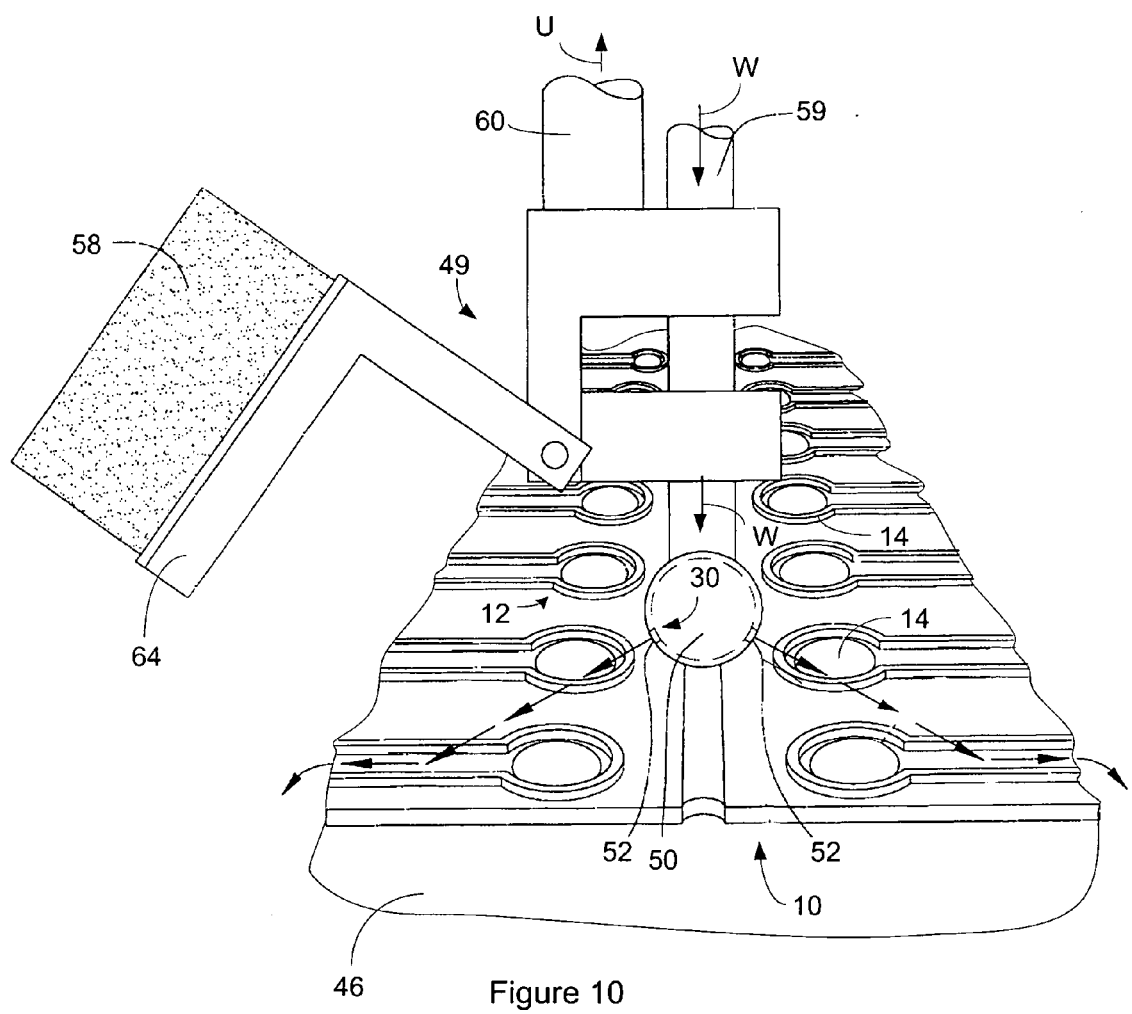
FIG. 10 is a side perspective view of the wash system of FIG. 7 washing a sensor structure.

As illustrated in FIG. 10, the arm 60 can continue to rise while the stream 31 of wash liquid strikes progressively closer to an edge of the sensor structure and washes away non-specifically bound compounds and excess wash liquid from the sensor structure.

Figure 11:
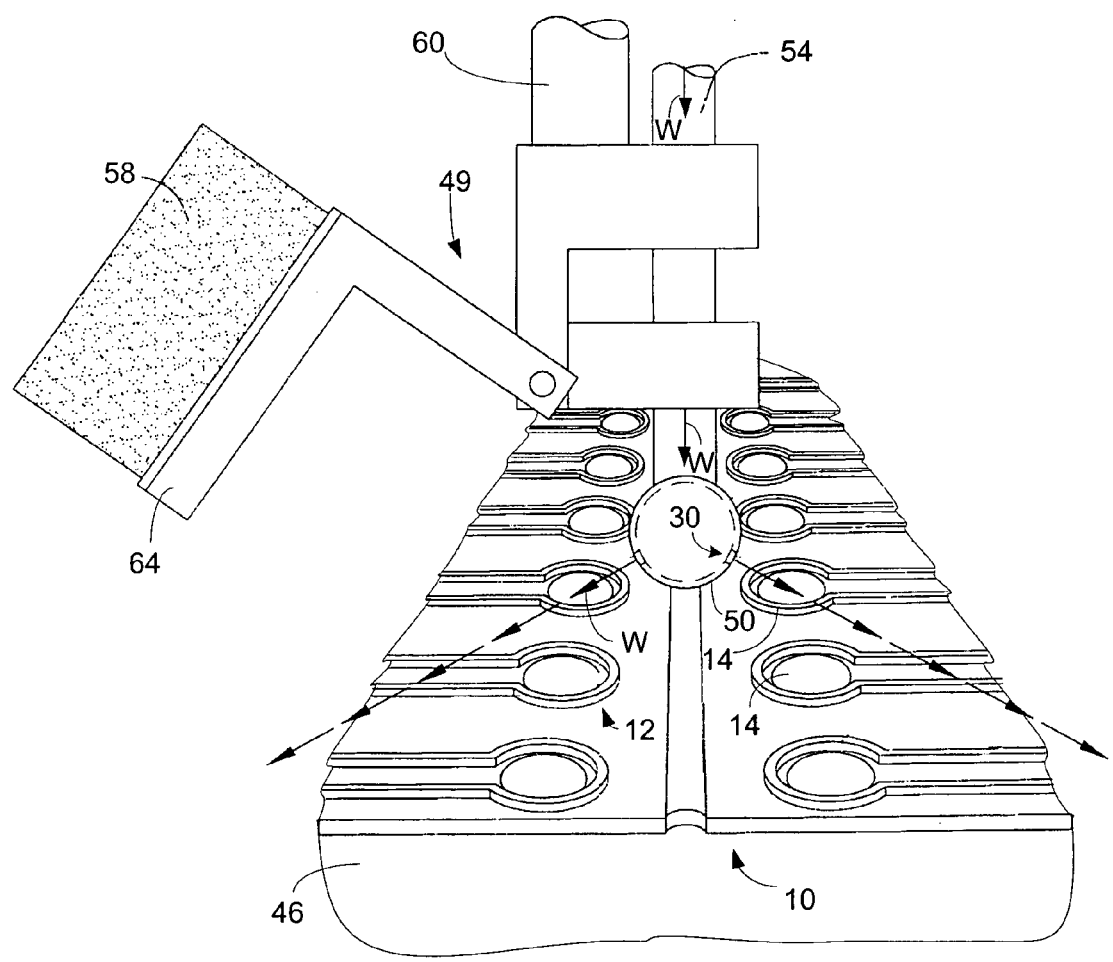
FIG. 11 is a side perspective view of the wash system of FIG. 7 washing a sensor structure.
Figure 12:
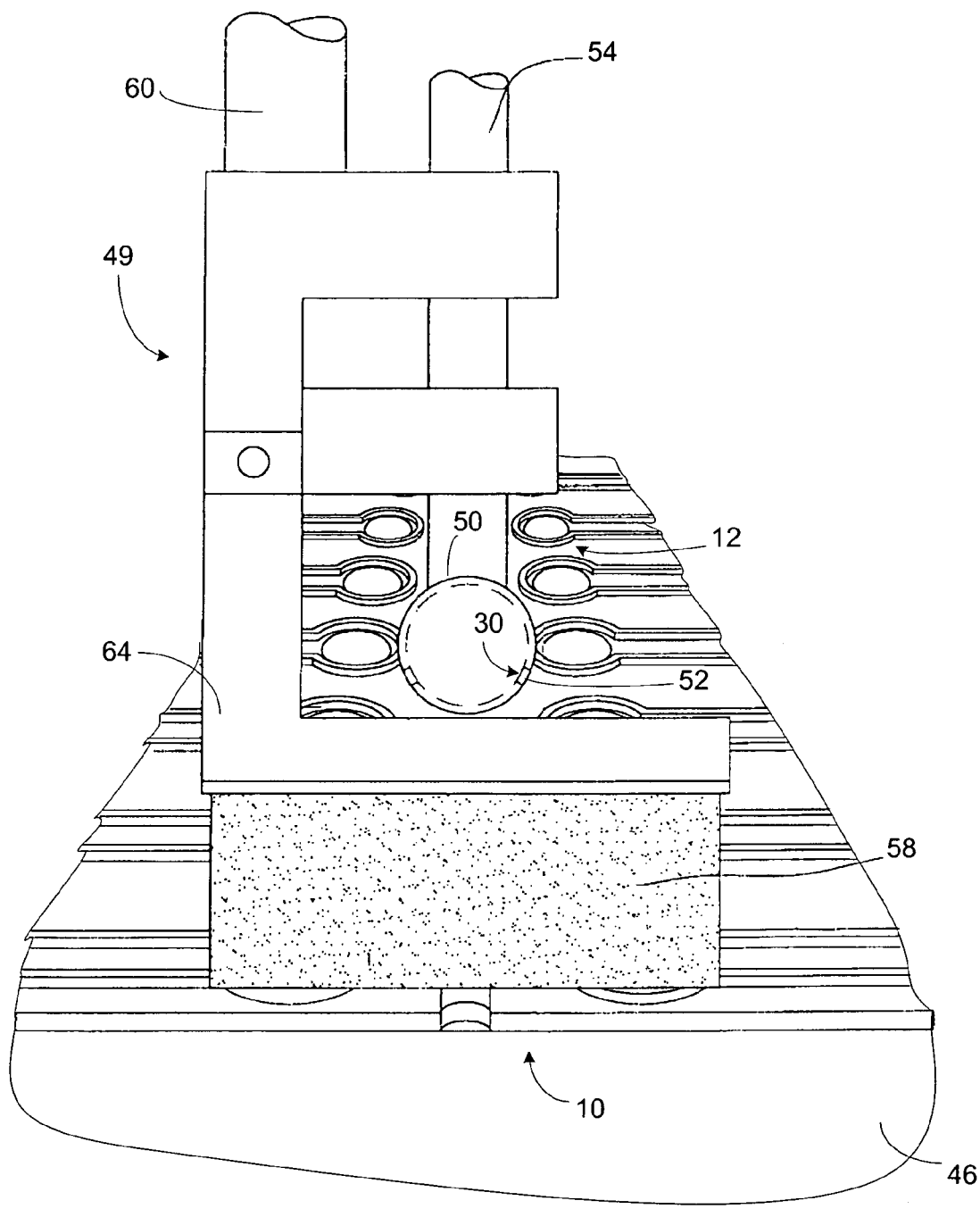
FIG. 12 is a perspective view of the wash system of FIG. 7. A sponge included in the wash system is applied to a sensor structure.

As illustrated in FIG. 11, the arm 60 can optionally continue to rise until the streams 31 of wash liquid no longer strikes the sensor structure. Subsequently, the wash liquid is stopped and the sponge 56 is moved into position over the sensor structure as shown in FIG. 12. For instance, the sponge 56 can be positioned in a holder 64 that is hinged to the wash source 49. The holder 64 can be manually or electronically moved such that the sponge 56 is located over the sensor structure. The arm 60 can be lowered to press the sponge 56 onto the surface of the sensor structure. The bottom of the sponge 56 can be contoured such that the sponge 56 contacts particular areas of the sensor structure without contacting other areas of the sensor structure. For instance, the bottom of the sponge 56 can be contoured such that the sponge 56 contacts particular electrodes on the sensor structure without contacting other electrodes, or such that the sponge 56 does not contact any of the electrodes and contacts areas around the electrodes, or such that the sponge 56 does not contact any of the sensors and contacts areas adjacent to the sensors. The sponge 56 wicks away the wash liquid and other materials from the contacted areas of the sensor structure. Subsequently, the arm 60 is raised, and the sponge 56 is rotated out of position with the sensor structure.

Figure 13:
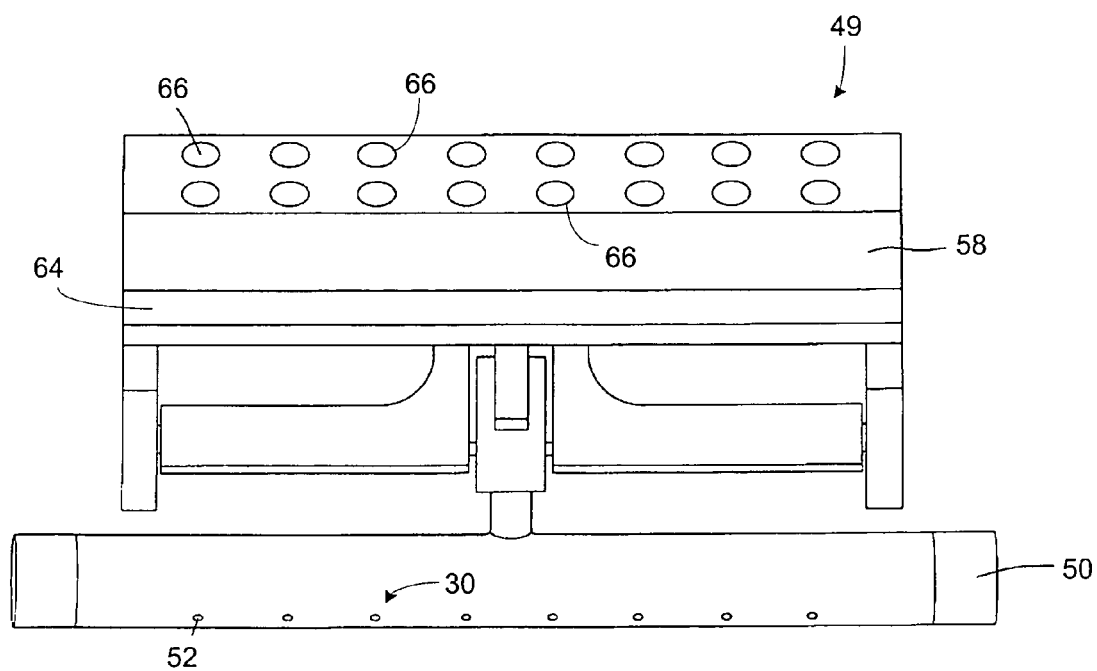
FIG. 13 is a side view of the wash system of FIG. 7 that shows the sponge and water outlet.
Figure 14:
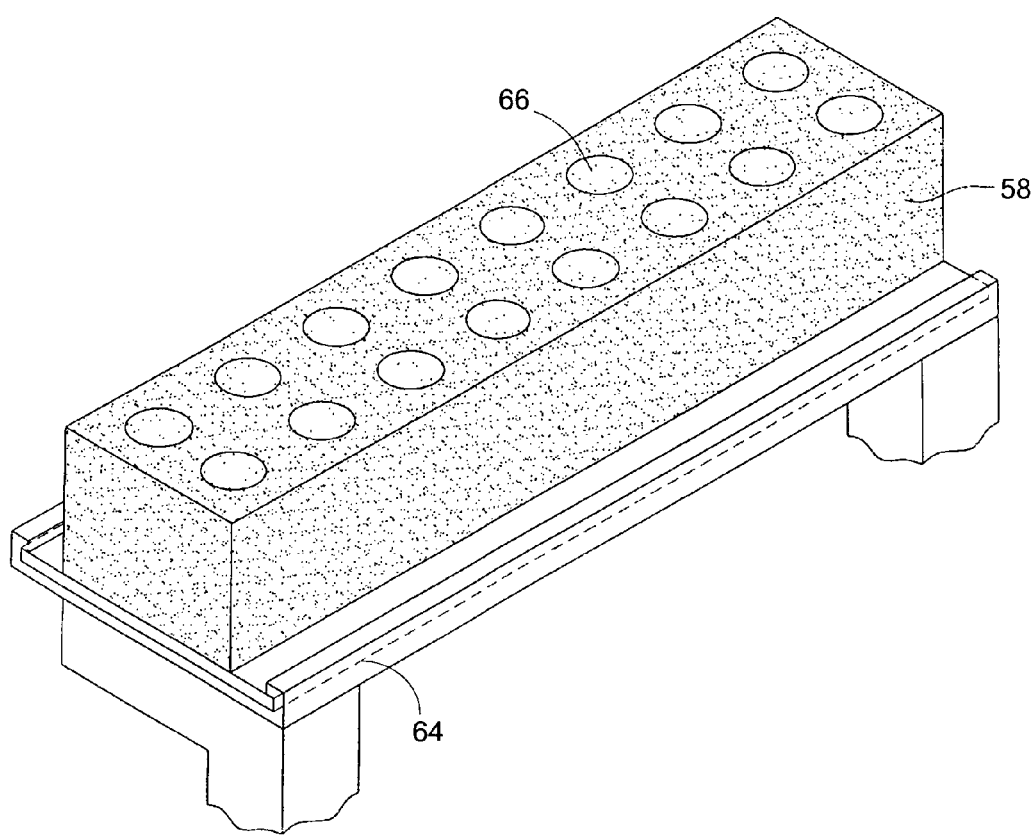
FIG. 14 is a perspective close-up view of a sponge included in the wash system of FIG. 7.

FIG. 13 and FIG. 14 illustrate the contours on the bottom of the sponge 56. FIG. 13 is a side perspective view of the wash source 49 of FIG. 7 through FIG. 12. FIG. 14 is a perspective view of the sponge 56 included in the wash system of FIG. 7. The sponge 56 includes a plurality of recesses 66 or holes. The recesses 66 can be slightly larger in diameter than the diameter of the sensors and can be positioned such that when the sponge 56 is applied to the sensor structure the sensors or particular electrodes are positioned in the recesses 66. As a result, the sponge 56 wicks away the wash liquid and other materials from the sensor structure without touching or contaminating the material on the sensors or particular electrodes.

A possible method for the wash system according to FIG. 7 through FIG. 14 can include all or a portion of the following acts: moving the liquid absorbing medium so the liquid absorbing medium does not receive the streams 31; move the wash source 49 toward the sensor structure such that streams 31 will each be received at a desired location on the sensor structure; generate the streams 31; increase the vertical distance between the sensor structure and the wash source 49 so as to move the location where each stream 31 is incident upon the sensor structure toward an edge of the sensor structure; stop the generation of the streams 31; move the liquid absorbing medium into a position over the sensor structure; move the liquid absorbing medium into contact with the sensor structure; wait a period of time sufficient for the liquid absorbing medium to absorb the wash liquid from the sensor structure; and repeat. These acts can be performed in the sequence disclosed above or in an alternate sequence.

Figure 15:
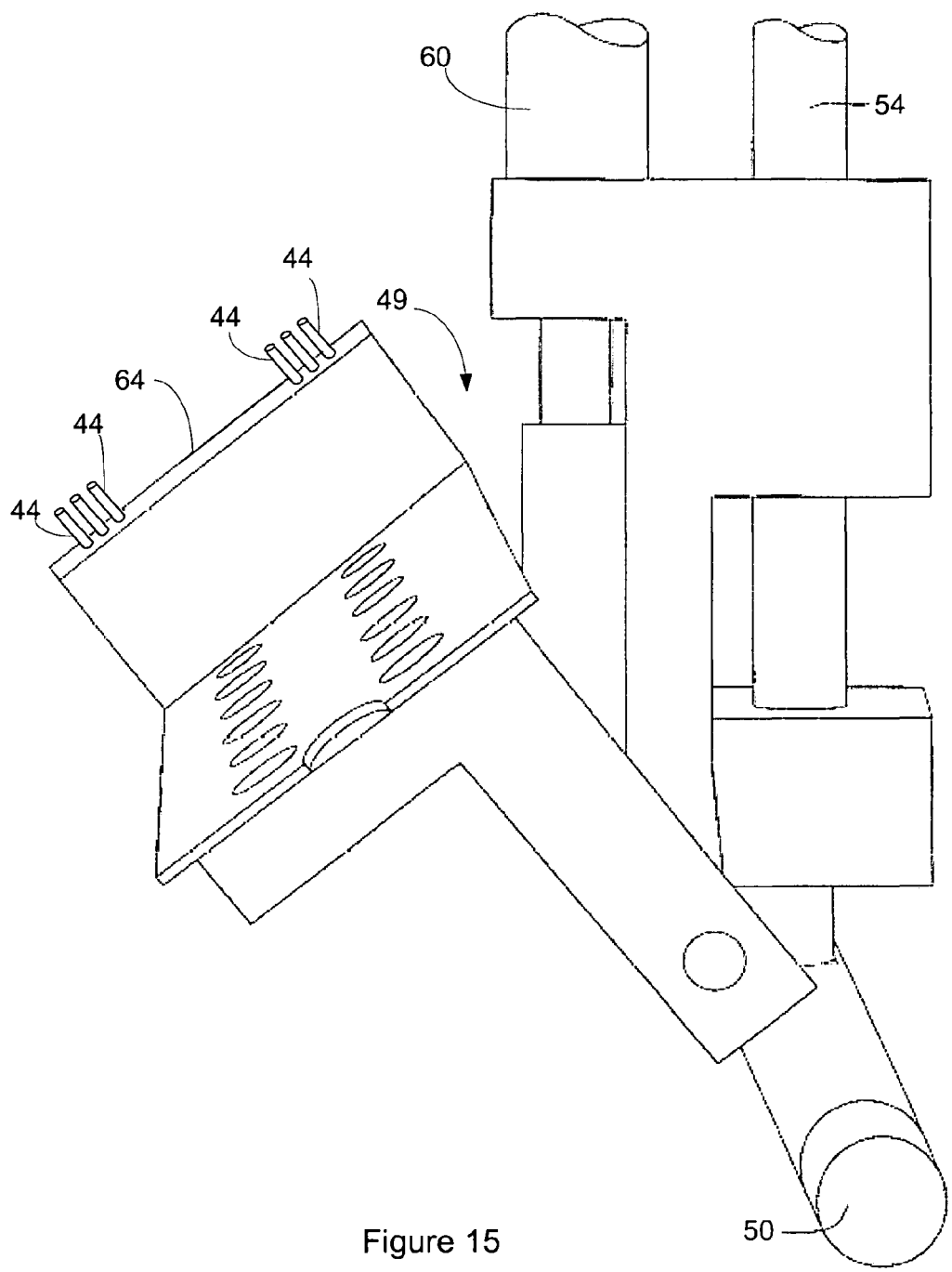
FIG. 15 is a perspective view of a wash system that includes vacuum tubes configured to apply a vacuum to a sensor structure.

FIG. 15 is a perspective view of a wash system where the wash source 49 includes gas conduits 44 mounted in a movable holder 64 that is connected to an arm 60. The holder 64 can permit the gas conduits 44 to be moved relative to the arm 60 and/or relative to the conduit 50. The wash source 49 can be configured to blow a through the gas conduits 44 and/or to pull a vacuum through the gas conduits 44.

Figure 16:
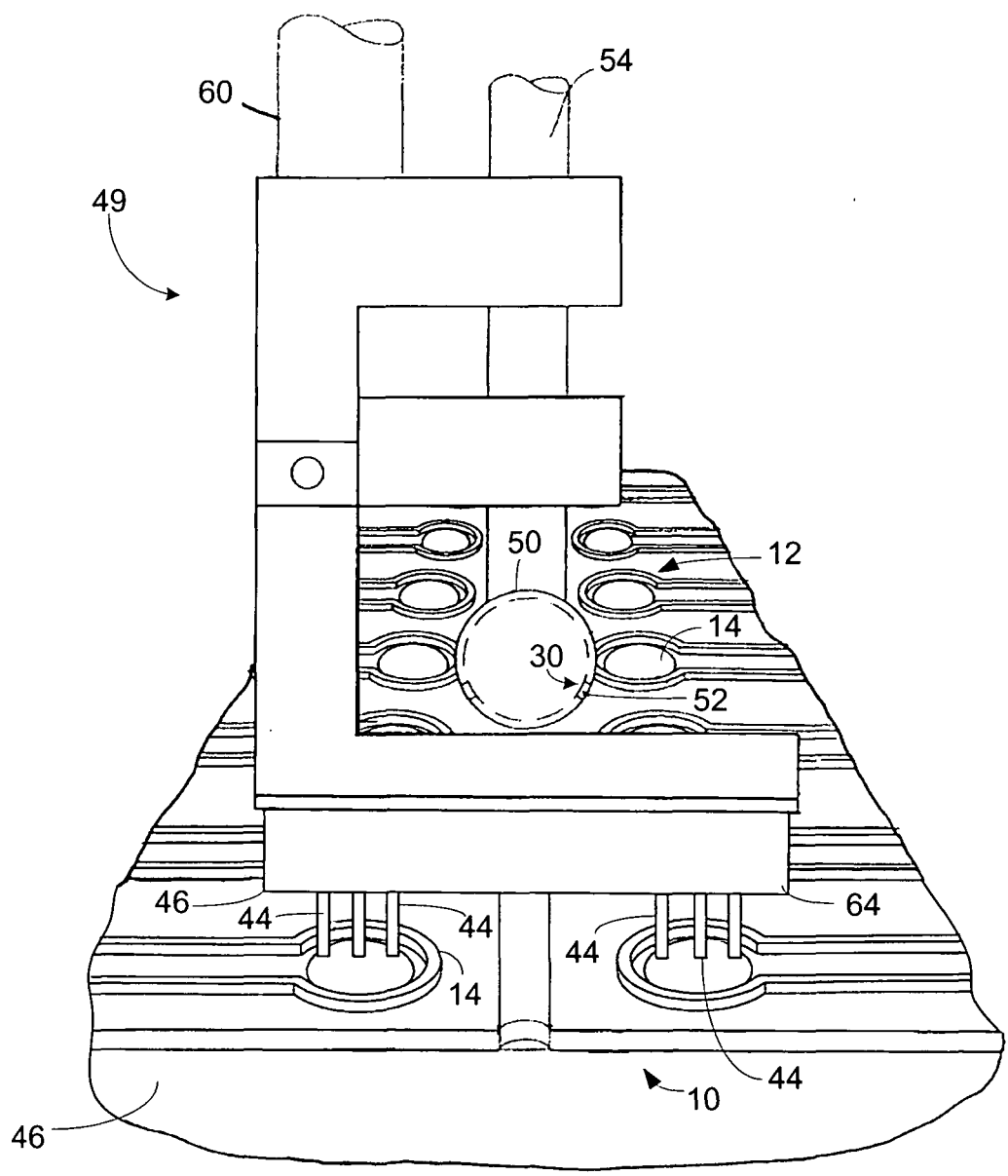
FIG. 16 is a side perspective view of the wash system of FIG. 15. The vacuum tubes are employed to apply a vacuum to a sensor structure.
Figure 17:
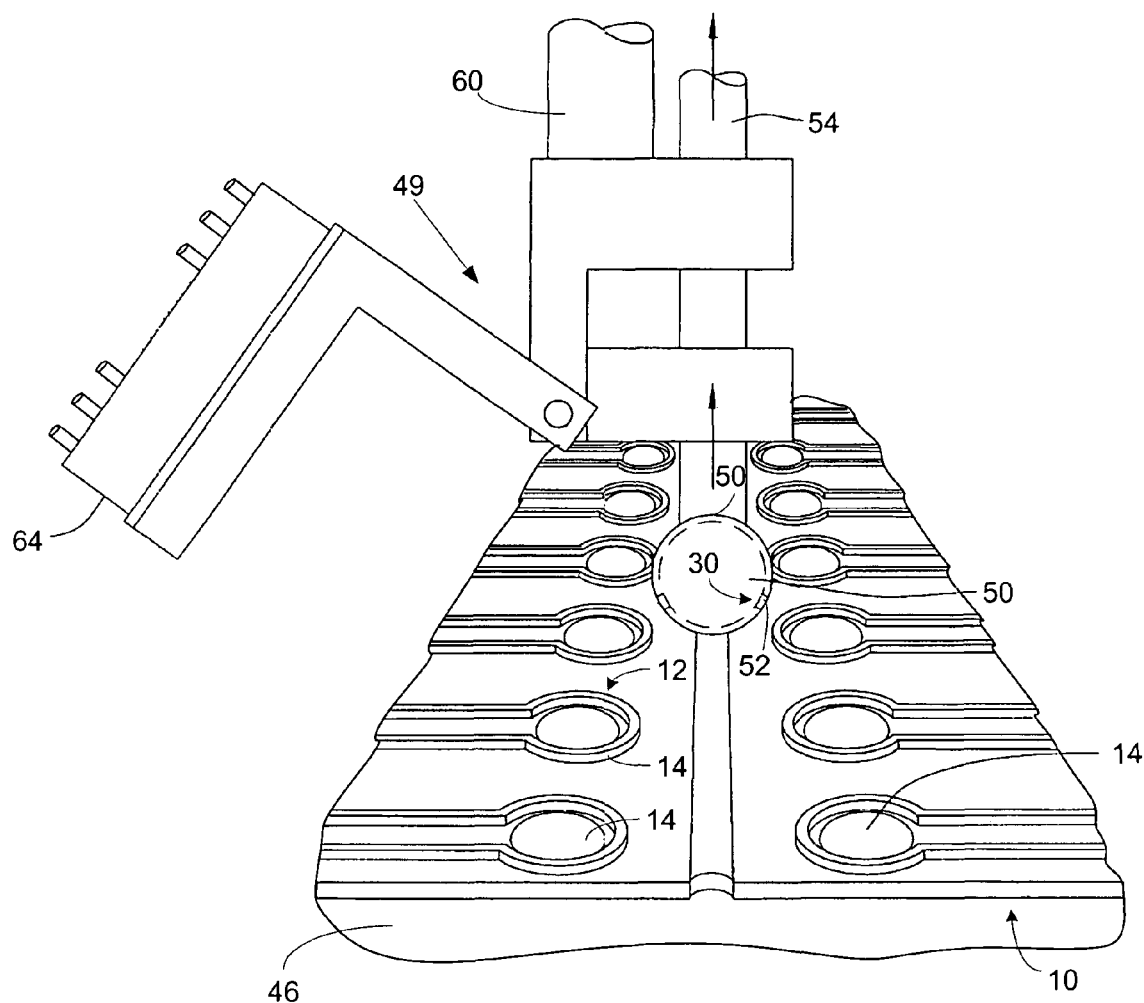
FIG. 17 is a side perspective view of the wash system of FIG. 15. The vacuum tubes are withdrawn from the sensor structure.

FIG. 16 and FIG. 17 illustrate the operation of the wash system of FIG. 15. The streams 31 of wash liquid can be sprayed onto the sensor structure as described with respect to FIG. 8 through FIG. 12. Subsequent to stopping the streams 31 of wash liquid, the holder 64 can be moved such that the gas conduits 44 are positioned over the sensor structure as shown in FIG. 16. For instance, the holder 64 can be manually or electronically moved such that the gas conduits 44 are positioned over the sensor structure. In particular, the holder 64 can be moved such that the gas conduits 44 are positioned over one or more of the electrodes on the sensor structure. In the event that the movement of the holder 64 does not achieve the desired horizontal alignment between the gas conduits 44 and the sensor structure, the wash system can move the holder 46 and/or the wash source 49 to achieve the desired horizontal alignment. Additionally or alternately, the arm 60 can also be up and/or down to achieve the desired distance between the gas conduits 44 and the sensor structure. After the gas conduits 44 are aligned with the desired location on the sensor structure, a vacuum can be drawn through the gas conduits 44 in order to vacuum wash liquid from the sensor structure. Additionally or alternately, a gas can be blown through the gas conduits 44 to blow wash liquid off of the sensor structure and/or to dry the sensor structure.

The arm 60, holder 46 and/or wash source 49 can be moved to sequentially achieve alignment of the gas conduits 44 with different locations on the sensor structure. For instance, the gas conduits 44 can be sequentially aligned with different sensors and then used to blow and/or vacuum each of the sensors. Alternately, the gas conduits 44 can be sequentially aligned with different electrodes and then used to blow and/or vacuum each of the electrodes.

After alignment of the gas conduits 44 with the different locations on the sensor structure, the arm 60 can be raised and/or the holder 64 can be moved such that the gas conduits 44 are no longer positioned over the sensor structure.

A possible method for the wash system according to FIG. 15 through FIG. 17 can include all or a portion of the following acts: moving the gas conduits 44 so the gas conduits 44 and/or holder 64 does not receive the streams 31; move the wash source 49 toward the sensor structure such that streams 31 will each be received at a desired location on the sensor structure; generate the streams 31; increase the vertical distance between the sensor structure and the wash source 49 so as to move the location where each stream 31 is incident upon the sensor structure toward an edge of the sensor structure; stop the generation of the streams 31; move the gas conduits 44 over the sensor structure; blow a gas onto on or more electrodes on the sensor structure and/or apply a vacuum to one or more electrodes on the sensor structure (this act can include one or more movements of the sensor structure relative to the one or more gas conduits 44 in order to sequentially align the electrodes and the gas conduits 44); repeat. These acts can be performed in the sequence disclosed above or in an alternate sequence Although FIG. 15 through FIG. 17 illustrate the wash system as having multiple gas conduits 44, the wash system can have a single gas conduit 44 that is aligned with a sequence of locations on the sensor structure. Additionally, FIG. 16 illustrates multiple gas conduits 44 aligned with a single electrode or a single sensor, however, the gas conduits 44 can be arranged such that a single gas conduits 44 is aligned with an electrode or a sensor.

Although FIG. 15 through FIG. 17 illustrate the wash system as not having a liquid absorbing medium such as a sponge 56, the wash system can include one or more gas conduits 44 and a liquid absorbing medium.

The one or more gas conduits can be used as an alternative to a liquid absorbing medium or in addition to a liquid absorbing medium.

In an exemplary embodiment, the wash systems are programmable in order to optimize the washing process for particular arrangements of sensors on the sensor structure, reagents, and/or soluble components. As discussed, the wash systems may be programmable to adjust the spraying angle $\theta$ relative to the surface of the sensor structure. The wash system may be programmed for the following:
 (1) wash liquid flow rate may vary between 0.1 ml/sec per sensor to 10 ml/sec per sensor, with one embodiment having a flow rate of 1 ml/sec per sensor;
 (2) wash time for spraying the wash liquid may vary between 0.1 seconds and 60 seconds, with one embodiment having a wash time of 3 seconds;
 (3) arm raising velocity may vary between 0.1 inch/sec to 10 inch/sec, with one embodiment having an arm raise velocity of 1 inch/sec;
 (4) arm raising pattern may rise up at a fixed speed, up with acceleration or variable speed; up and down cycling with fixed speed; and up and down cycling with variable speed; and
 (5) flow rate pattern may be fixed, pulsing, or with acceleration.

The wash systems are further adapted for manual adjustment of the nozzle 30/hole spray angle, which may vary between 5° and 80°, with one embodiment having a nozzle 30/hole spray angle of 40°.

Figure 18:
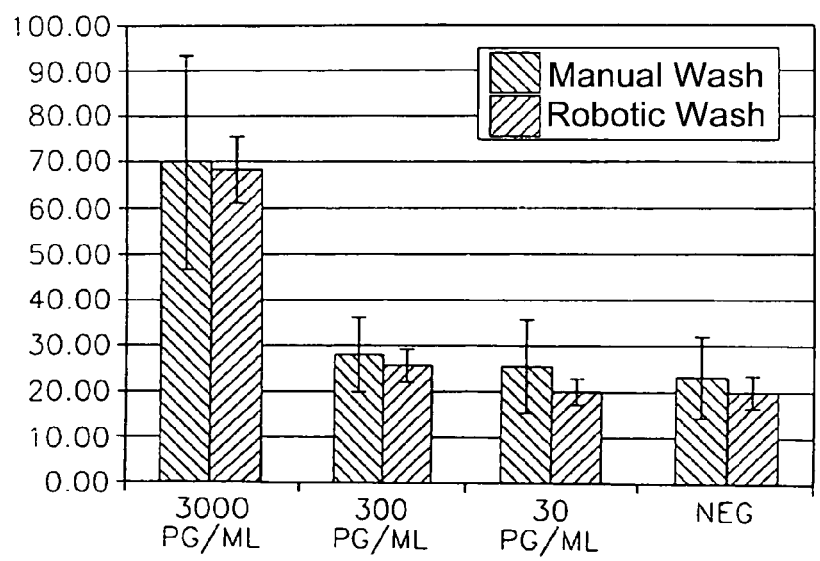
FIG. 18 sets forth data showing signal variance reduction improvement of the wash system over manual washing.

FIG. 18 sets forth data showing signal variance reduction (% error) improvement of the wash system over manual washing. As shown in the graphs and chart, the wash system provides signal variance reduction improvement over manual washing and reduces the noise for overall signal-to-noise improvement. The improvement of the signal-to-noise ratio is especially significant when sample sizes are small.

A suitable wash liquid for use in the wash system includes, but is not limited to, deionized (DI) water, phosphate buffered saline (PBS) buffer with Tween, commercial Enzyme-Linked ImmunoSorbent Assay (ELISA) wash buffer, phosphate wash liquid, sodium dodecyl sulfate (SDS), sodium chloride/ sodium citrate (SSC) wash liquid, solvent wash liquid, detergent wash liquid, hybridization wash liquid, bitin wash liquid, or any combination of the above wash liquids. In some instances, the wash liquid can be selected based on the non-specifically bound compounds that are being targeted for removal, the mechanism by which the compound would bind to the sensor structure, and/or the sample matrix.

Examples of compounds that may non-specifically bind to the sensor structure itself or to other compounds on the sensor structure include, but are not limited to, macromolecules such as DNA, RNA and proteins or small molecules such as hormones, organic compounds, and drug molecules. As a result, the wash system can be employed to remove the non-specifically bound molecules of these compounds. Additionally, these compounds can be presented in different media such as blood, urine, saliva, cerebrospinal fluid (CSF), sputum, water, milk, food product, culture and diluent. Since the ionic strength, viscosity and/or impurity content are different in these different media, the washing efficiency and washing conditions can be different for different applications.

The sensor structure of FIG. 2 through FIG. 17 are shown as having multiple sensors where each sensor includes one or more electrodes. The illustrated wash systems can be used with a sensor structure having sensors constructed according to FIG. 1A through FIG. 1C.

The wash system and sensor structure are disclosed in the context of a sensor structure having multiple electrodes on a substrate. The electrodes can be a metal pad on the substrate. Preferably, the electrodes are a metal pad that is located on the substrate and is in electrical communication with a contact pad for applying electrical energy to the metal pad.

The wash system can include other components that are not illustrated. For instance, the wash system can include other components such as motors and electronics for causing movement and controlling movement of the different elements of the wash system such as a holder for the sensor structure and/or the wash source. The wash system can also includes one or more pumps for driving movement of the liquids employed by the wash system. The pumps can be operated by the electronics.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

What is claimed is:

1. A sensor wash system, comprising:
a sensor structure having multiple electrochemical sensors on a substrate, the sensors each being configured to detect a presence and/or amount of a compound on the sensor,
each of the electrochemical sensors including multiple electrodes,
the electrodes in each electrochemical sensor including a working electrode to which compounds are bound such that a portion of the compounds are specifically bound and another portion of the compounds are non-specifically bound;
a wash source concurrently generating a plurality of streams, different streams are each incident on a different one of the working electrodes such that the different streams each removes non-specifically bound compounds from the working electrode that receives the stream while leaving specifically bound compounds bound to the working electrode that receives the stream.

2. The system of claim 1, wherein the wash source is configured to concurrently scan the each of the streams across a surface of the working electrode that receives the stream.

3. The system of claim 1, wherein the wash source generates the streams such that an angle of incidence between each stream and the electrode that receives the stream is in a range of greater than or equal to 5° and less than or equal to 80°.

4. The system of claim 1, wherein the wash source generates the streams such that the streams are concurrently incident on different working electrodes.

5. The system of claim 1, wherein the wash source includes a plurality of nozzles and is configured to generate the streams such that each stream exits from a different one of the nozzles and the wash source is configured to move the stream sources vertically relative to the electrodes.

6. The system of claim 1, wherein the wash source includes a plurality of nozzles and is configured to generate the streams such that each stream exits from a different one of the nozzles and the wash source is configured to move the stream sources vertically relative to the electrodes such that the movement of the stream sources is concurrent with the incidence of the streams on the electrodes.

7. The system of claim 1, wherein the wash source includes one or more gas conduits that are each configured to vacuum a liquid off one of the sensors.

8. The system of claim 1, wherein the wash source includes one or more gas conduits that are each configured to apply vacuum suction to one of the electrodes, and
different vacuum tubes are configured to concurrently apply the vacuum suction to a different one of the electrodes.

9. The system of claim 1, wherein the wash source includes one or more gas conduits that are each configured to blow a gas onto one of the electrodes.

10. The system of claim 1, wherein each of the sensors is configured to generate electrical current from a chemical reaction in a solution and/or to use electrical energy to cause a chemical reaction in the solution.

11. The system of claim 1, wherein the non-specifically bound compounds are bound to the working electrode with hydrogen bonds and the specifically bound compounds are bonded to the working electrode with covalent bonds.

12. The system of claim 1, wherein the non-specifically bound compounds include a component selected from a group consisting of DNA, RNA, proteins, and hormones.

13. The system of claim 12, wherein the wash source concurrently scans each of the streams across a surface of the working electrode that receives the stream,
an angle of incidence between each stream and the electrode that receives the stream is in a range of greater than or equal to 5° and less than or equal to 80°,
the streams are concurrently incident on different working electrodes.

14. The system of claim 13, wherein the wash source includes sources of each stream and the wash source is configured moves the stream sources vertically relative to the working electrodes.

15. The system of claim 14, wherein the wash source includes one or more gas conduits and employs the gas conduits to vacuum a liquid off one of the sensors.

16. The system of claim 14, wherein the wash source includes one or more gas conduits employs different gas conduits to concurrently vacuum liquid off different working electrodes.

17. The system of claim 16, wherein the wash source employs different gas conduits to blow a gas onto the working electrodes.

18. A method of operating a wash system, comprising:
concurrently spraying streams of a wash liquid onto a sensor structure having multiple electrochemical sensors on a substrate,
- the sensors each being configured to detect a presence and/or amount of a compound on the sensor,
- each of the electrochemical sensors including multiple electrodes,
- the electrodes in each electrochemical sensor including a working electrode to which compounds are bound such that a portion of the compounds are specifically bound and another portion of the compounds are non-specifically bound,
- the streams being sprayed such that each one of the streams is incident on a different one of the working electrodes such that the different streams each removes non-specifically bound compounds from the working electrode that receives the stream while leaving specifically bound compounds bound to the working electrode that receives the stream, and
- each of the streams being incident on one of the electrodes at an angle that is non-perpendicular to the sensor.

19. The method of claim 18, further comprising:
vacuuming wash liquid off of the electrodes after spraying the streams of the wash liquid onto the sensor structure.

20. The method of claim 18, further comprising:
blowing a gas onto the electrodes after spraying the streams of the wash liquid onto the sensor structure.

21. The method of claim 20, wherein of the electrochemical sensors are each configured to generate electrical current from a chemical reaction in a solution and/or to use electrical energy to cause a chemical reaction in the solution.

22. The method of claim 18, further comprising:
concurrently scanning the streams across a surface of each of the electrodes that receives one of the streams.

\* \* \* \* \*